United States Patent [19]
Page et al.

[11] Patent Number: 5,277,177
[45] Date of Patent: * Jan. 11, 1994

[54] SINGLE USE MEDICAL ASPIRATING DEVICE AND METHOD

[75] Inventors: Larry E. Page, Salt Lake City; Darrel Palmer, Sandy, both of Utah

[73] Assignee: Ballard Medical Products, Draper, Utah

[*] Notice: The portion of the term of this patent subsequent to Feb. 11, 2003 has been disclaimed.

[21] Appl. No.: 730,743

[22] Filed: Jul. 16, 1991

Related U.S. Application Data

[60] Division of Ser. No. 679,703, Apr. 3, 1991, abandoned, which is a division of Ser. No. 484,589, Feb. 23, 1990, abandoned, which is a division of Ser. No. 28,805, Mar. 23, 1987, abandoned, which is a continuation-in-part of Ser. No. 917,866, Oct. 14, 1986, abandoned, and a continuation-in-part of Ser. No. 916,341, Oct. 7, 1986, Pat. No. 4,696,296, which is a division of Ser. No. 767,400, Aug. 20, 1985, Pat. No. 4,638,539, which is a division of Ser. No. 633,570, Jul. 23, 1984, Pat. No. 4,569,344.

[51] Int. Cl.⁵ ............................................. A61M 16/00
[52] U.S. Cl. ..................... 128/200.26; 128/207.14; 128/207.16
[58] Field of Search ............... 128/200.26, 207.14, 128/207.15, 207.16; 251/335.2

[56] References Cited

U.S. PATENT DOCUMENTS

| | | | |
|---|---|---|---|
| 113,503 | 4/1871 | Dinnen | 251/335.2 |
| 274,447 | 3/1883 | Kennish | 604/250 |
| 580,574 | 4/1897 | Fowler | 251/100 |
| 1,120,549 | 12/1914 | Schellberg | 604/171 |
| 1,463,735 | 7/1923 | Varrieur | 251/100 |
| 1,672,114 | 6/1928 | Crow | 604/249 |
| 1,917,981 | 7/1933 | Kindl | 251/95 |
| 1,944,553 | 1/1934 | Freund | 604/249 |
| 2,187,586 | 1/1940 | Hooper | 604/249 |
| 2,212,334 | 8/1940 | Wallerich | 264/330 |
| 2,289,721 | 7/1942 | Mueller | 251/335.2 |
| 2,584,450 | 2/1952 | Holt et al. | 128/200.13 |
| 2,705,959 | 4/1955 | Elmore | 128/207.14 |
| 2,734,773 | 2/1956 | Ivins | 251/335.2 |
| 2,735,590 | 2/1956 | Ayres | 251/335.2 |
| 2,755,060 | 7/1956 | Twyman | 251/342 |
| 2,776,105 | 1/1957 | Schmitz | 251/335.2 |
| 2,893,395 | 7/1959 | Buck | 604/283 |
| 2,895,708 | 7/1959 | Palumbo | 251/77 |
| 2,912,982 | 11/1959 | Barsky | 128/207.14 |
| 2,924,212 | 2/1960 | Michaels | 137/315 |
| 2,937,643 | 5/1960 | Elliot | 604/163 |
| 3,017,880 | 1/1962 | Brook | 128/203.11 |
| 3,039,463 | 6/1962 | Dickey, Jr. et al. | 604/119 |
| 3,070,132 | 12/1962 | Sheridan | 138/118 |
| 3,104,090 | 9/1963 | Callahan, Jr. | 251/278 |
| 3,175,557 | 3/1965 | Hammond | 128/207.14 |
| 3,207,472 | 9/1965 | Sellsam | 251/331 |
| 3,322,126 | 5/1967 | Rüsch et al. | 128/207.15 |
| 3,335,723 | 8/1967 | Waldman, Jr. | 604/163 |
| 3,363,629 | 1/1968 | Kuhn | 128/207.15 |
| 3,444,860 | 5/1968 | Harrell | 128/767 |
| 3,461,877 | 8/1969 | Morch | 128/207.14 |
| 3,485,234 | 12/1969 | Stevens | 128/657 |
| 3,508,554 | 4/1970 | Sheridan | 604/280 |
| 3,517,669 | 6/1970 | Buono et al. | 604/119 |
| 3,584,834 | 6/1971 | Reid et al. | 251/335.2 |
| 3,595,445 | 7/1971 | Burford et al. | 222/213 |

(List continued on next page.)

FOREIGN PATENT DOCUMENTS 8102675 10/1981 PCT Int'l Appl. ............ 128/207.15

Primary Examiner—Edgar S. Burr
Assistant Examiner—Aaron J. Lewis
Attorney, Agent, or Firm—Lynn G. Foster

[57] ABSTRACT

A reliable contamination resistant single use disposable medical non-ventilating aspirating device and method. The device releasibly connects to and aligns with an indwelling endotracheal tube to accommodate advancing of an aspirating catheter tube of the device by manual manipulation through a sterile flexible envelope and selective evacuation of lung secretions through a closed and sterile two-position normally closed manually operable valve at the proximal end of the device, while simultaneously accommodating voluntarily respiration by the patient.

19 Claims, 6 Drawing Sheets

U.S. PATENT DOCUMENTS

| | | | |
|---|---|---|---|
| 3,605,750 | 9/1971 | Sheridan et al. | 128/658 |
| 3,612,038 | 10/1971 | Halligan | 128/658 |
| 3,614,057 | 10/1971 | Hospe | 251/251 |
| 3,628,532 | 12/1971 | Magrath | 128/204.17 |
| 3,633,758 | 1/1972 | Morse | 211/13 |
| 3,719,737 | 3/1973 | Vaillancourt | 264/162 |
| 3,730,179 | 5/1973 | Williams | 128/204.18 |
| 3,734,094 | 5/1973 | Calinog | 128/642 |
| 3,757,771 | 9/1973 | Ruegg et al. | 128/635 |
| 3,774,604 | 11/1973 | Danielsson | 604/169 |
| 3,825,001 | 7/1974 | Bennet et al. | 604/170 |
| 3,885,561 | 5/1975 | Cami | 604/247 |
| 3,894,540 | 7/1975 | Bonner, Jr. | 604/171 |
| 3,902,500 | 9/1975 | Dryden | 128/207.14 |
| 3,911,910 | 10/1975 | Raitto | 602/2 |
| 3,935,857 | 2/1976 | Co | 128/658 |
| 3,937,220 | 2/1976 | Coyne | 604/119 |
| 3,991,762 | 11/1976 | Radford | 128/207.16 |
| 4,015,336 | 4/1977 | Johnson | 433/95 |
| 4,022,219 | 5/1977 | Basta | 128/207.14 |
| 4,027,659 | 6/1977 | Slingluff | 128/658 |
| 4,032,106 | 6/1977 | Schieser et al. | 251/335.2 |
| 4,036,210 | 7/1977 | Campbell et al. | 128/768 |
| 4,047,527 | 9/1977 | Kelsen | 604/83 |
| 4,050,667 | 9/1977 | Kossell | 249/82 |
| 4,052,990 | 10/1977 | Dodgson | 128/207.14 |
| 4,062,363 | 12/1977 | Bonner, Jr. | 604/171 |
| 4,081,176 | 3/1978 | Johnson | 251/342 |
| 4,119,101 | 10/1978 | Igich | 128/202.16 |
| 4,122,591 | 10/1978 | Kramann et al. | 29/890.12 |
| 4,152,017 | 5/1979 | Abramson | 285/260 |
| 4,170,996 | 10/1979 | Wu | 604/171 |
| 4,193,406 | 3/1980 | Jinotti | 128/204.18 |
| 4,212,300 | 7/1980 | Meals | 604/119 |
| 4,225,371 | 9/1980 | Taylor et al. | 156/152 |
| 4,235,232 | 11/1980 | Spaven et al. | 604/178 |
| 4,240,417 | 12/1980 | Holevel | 128/203.12 |
| 4,245,636 | 1/1981 | Sparky et al. | 604/249 |
| 4,256,099 | 3/1981 | Dryden | 128/200.26 |
| 4,275,724 | 6/1981 | Behrstock | 128/207.14 |
| 4,280,680 | 7/1981 | Payne | 251/335.2 |
| 4,300,550 | 11/1981 | Gandi et al. | 128/207.18 |
| 4,324,239 | 4/1982 | Gordon et al. | 604/122 |
| 4,326,520 | 4/1982 | Alley | 604/171 |
| 4,327,723 | 5/1982 | Frankhouser | 604/171 |
| 4,327,735 | 5/1982 | Hampson | 604/171 |
| 4,356,610 | 11/1982 | Hon et al. | 29/428 |
| 4,387,879 | 7/1983 | Tauschinski | 251/149.1 |
| 4,397,442 | 8/1983 | Larkin | 251/342 |
| 4,414,999 | 11/1983 | Basta | 137/240 |
| 4,426,062 | 1/1984 | Bowiom | 251/7 |
| 4,440,378 | 4/1984 | Sullivan | 251/117 |
| 4,451,257 | 5/1984 | Atchley | 604/119 |
| 4,456,223 | 6/1984 | Ebling | 251/342 |
| 4,457,487 | 7/1984 | Steigerwald | 251/117 |
| 4,459,982 | 7/1984 | Fry | 128/204.23 |
| 4,469,483 | 9/1984 | Becker et al. | 604/280 |
| 4,497,468 | 2/1985 | Hubbard et al. | 251/117 |
| 4,510,933 | 4/1985 | Wendt et al. | 128/207.14 |
| 4,534,542 | 8/1985 | Russo | 251/342 |
| 4,537,387 | 8/1985 | Danby et al. | 251/331 |
| 4,569,344 | 2/1986 | Palmer | 128/910 |
| 4,595,005 | 6/1986 | Jinotti | 128/205.24 |
| 4,632,112 | 12/1986 | Matthews | 604/49 |
| 4,646,733 | 3/1987 | Stroh et al. | 128/207.16 |
| 4,655,752 | 4/1987 | Honkanen et al. | 604/256 |
| 4,671,291 | 6/1987 | Wilson | 128/658 |
| 4,673,393 | 6/1987 | Suzuki et al. | 604/167 |
| 4,696,305 | 9/1987 | von Berg | 128/673 |
| 4,703,775 | 11/1987 | Pastrone | 137/625.3 |
| 4,704,111 | 11/1987 | Moss | 604/270 |
| 4,805,611 | 2/1989 | Hodgkins et al. | 128/207.14 |
| 4,938,741 | 7/1990 | Lambert | 604/19 |
| 4,967,743 | 11/1990 | Lambert | 128/207.16 |

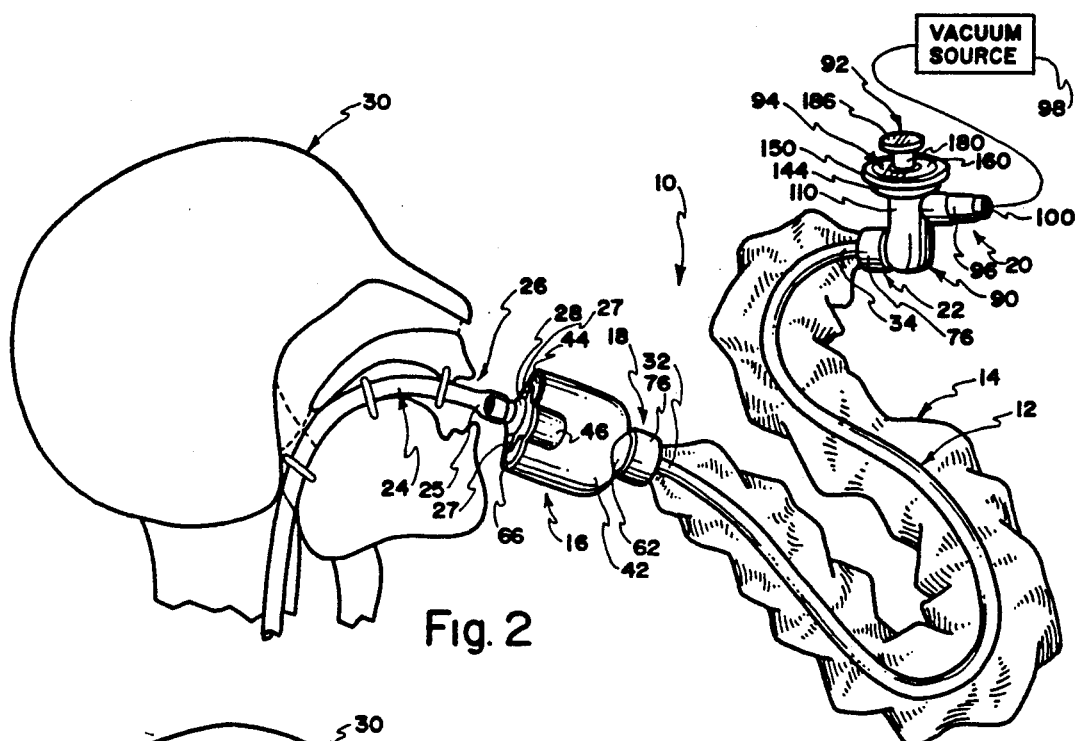
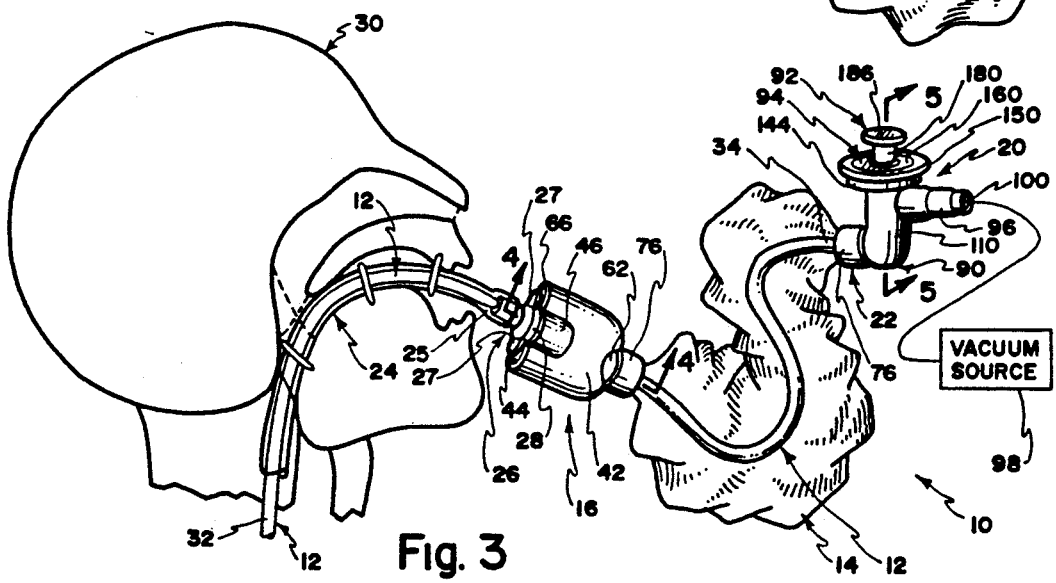

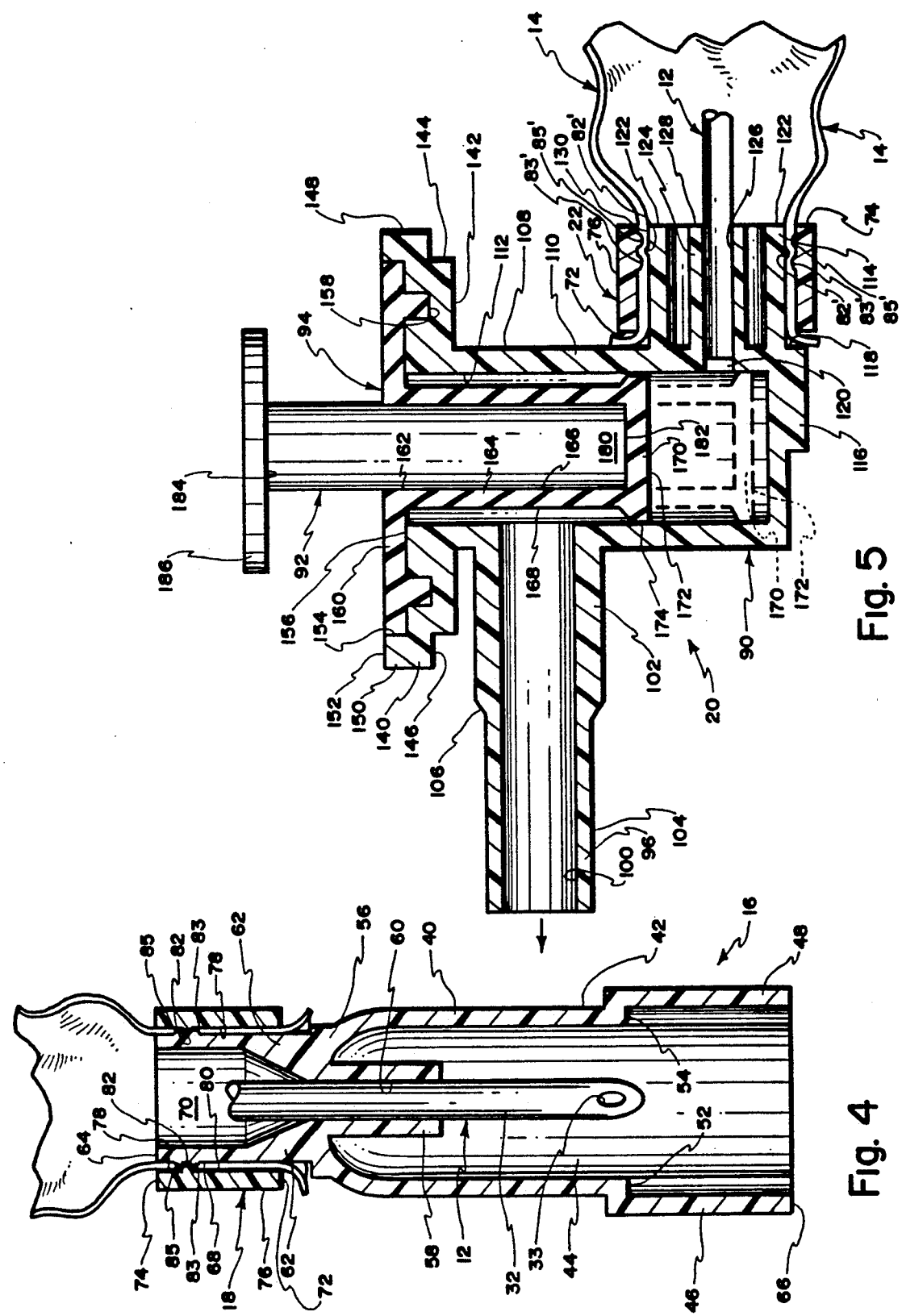

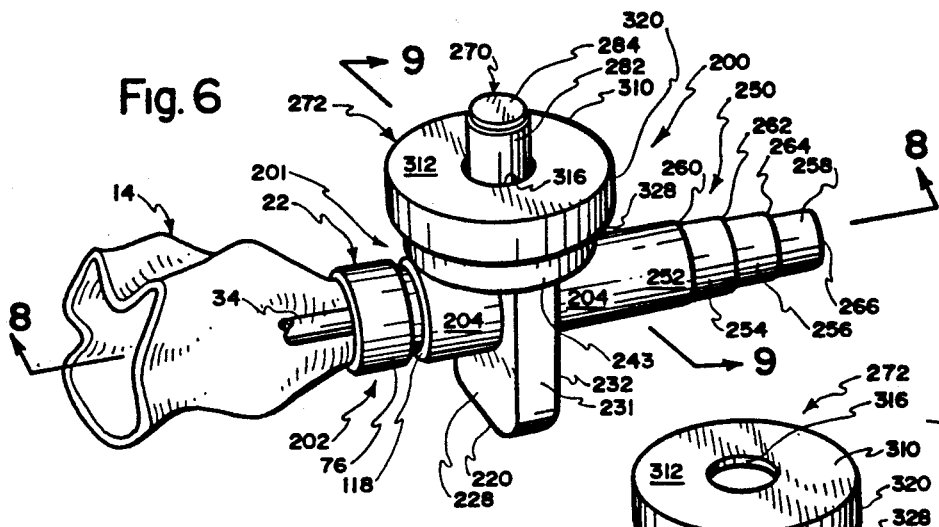
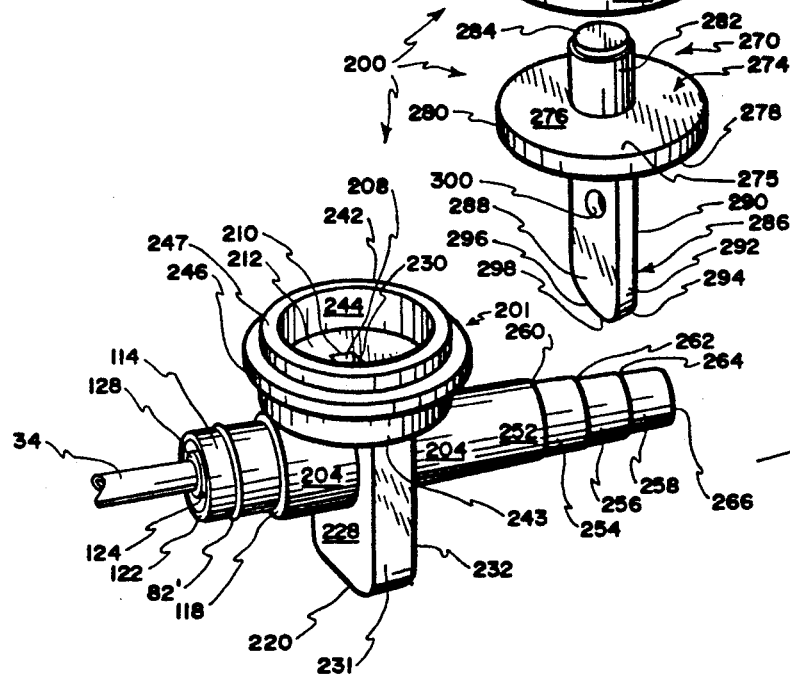

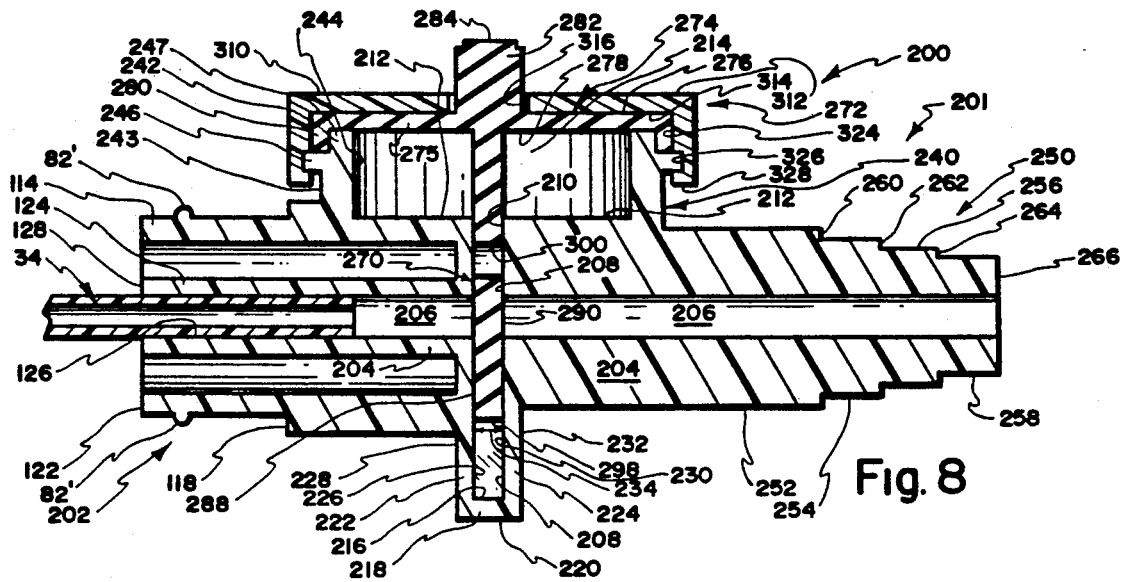
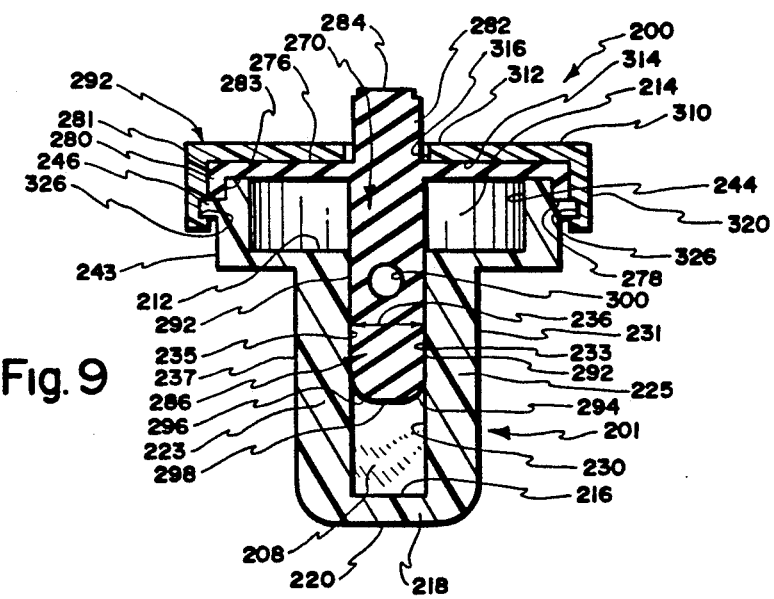

SINGLE USE MEDICAL ASPIRATING DEVICE AND METHOD

CONTINUITY

This application is a division of U.S. Ser. No. 679,703, filed Apr. 3, 1991, now abandoned, which is a division of U.S. Ser. No. 484,589, filed Feb. 23, 1990, now abandoned, which is a division of U.S. Ser. No. 28,805, filed Mar. 23, 1987, now abandoned, which is a continuation-in-part of U.S. Ser. No. 917,866, filed Oct. 14, 1986, now abandoned, and a continuation-in-part of U.S. Ser. No. 916,341, filed Oct. 7, 1986, now U.S. Pat. No. 4,696,296, which is a division of U.S. Ser. No. 767,400, filed Aug. 20, 1985, now U.S. Pat. No. 4,638,539, which is a division of U.S. Ser. No. 633,570, filed Jul. 23, 1984, now U.S. Pat. No. 4,569,344.

FIELD OF THE INVENTION

The present invention relates generally to aspiration of secretions from the lungs of medical patients and more particularly to a novel single use disposable aspirating device, and related method, the device being releasibly used in conjunction with an indwelling endotracheal tube in such a way that voluntary respiration is accommodated, the single use aspirating device functioning to remove accumulated secretions from the lungs of a medical patient.

PRIOR ART

The relevant, known aspirating prior art falls into two categories. The first category comprises combination ventilating and aspirating devices left connected to the patient for relatively long periods of time, during both intervals of use and non-use. U.S. Pat. Nos. 3,991,762 and 4,569,344 typify devices within the first category. These are closed involuntary ventilating systems. The presently preferred device of the present invention is of another type, i.e. an open voluntary respiratory system.

The second category comprises single use non-ventilating devices, such as Davol's aspirating catheter assembly, which comprises a sterile bag, a catheter tube within the bag and a vent fitting at the proximal end of the assembly, which is operated to aspirate by placing a thumb or finger over an atmospheric vent port. This type of device has serious deficiencies, such as risk of contamination through the atmospheric vent and awkwardness in the use thereof, given the detached nature of such, i.e. the lack of capacity of the device to be temporarily connected to and aligned with an indwelling endotracheal tube. Also, coughing by the patient during use of such a device contaminates areas outside the aspirating device per se.

BRIEF SUMMARY AND OBJECTS OF THE INVENTION

In brief summary, the present invention overcomes or substantially alleviates the deficiencies of the prior art by providing a reliable contamination resistant single use disposable non-ventilating medical aspirating device, one embodiment of which releasibly connects to and aligns with an indwelling endotracheal tube, in such a way that voluntary respiration is accommodated, by which an aspirating catheter tube of the device is facilely and accurately advanced, by manual manipulation through a collapsible sterile flexible envelope, into a desired lung of a patient and selectively evacuating lung secretions through the catheter tube and a closed and sterile two-position normally closed manually operable valve at the proximal end of the device. Contamination due to patient coughing during use of device is confined to the aspirating device itself. A related method is provided also. Structure is also provided for restraining the suction catheter tube in any desired extended position relative to the remainder of the aspirating device. This structure can also form a substantial seal against entry of contaminants into the interior of the envelope and applies to both aspirating and aspirating/ventilating systems. As used herein "non-ventilating" means having no capacity to force the patient to involuntarily ventilate.

Accordingly, it is a primary object of the present invention to provide a novel single use disposable medical aspirating device and a related method.

Another paramount object is the provision of a non-ventilating single use aspirating device which is reliable and contamination resistant.

A further important object of the present invention is the provision of a novel disposable medical aspirating device which is releasibly connected to and aligned with an indwelling endotracheal tube at the time of use.

Another dominant object is the provision of a non-ventilating aspirating device having a novel fitting at the distal end thereof for releasibly connecting and aligning the device with an indwelling endotracheal tube, while accommodating simultaneous voluntary respiration.

Still another significant object is the provision of a non-ventilating medical aspirating device having a novel manually operable normally closed valve at the proximal end thereof by which secretions are evacuated from the lungs of a medical patient through an aspirating catheter tube of the device.

A further primary object of the present invention is the provision of a novel disposable medical aspirating device comprising a manually operable normally closed contamination resistant valve at the proximal end of the device.

It is an additional significant object to provide a novel single use aspirating device for facilely and accurately advancing a catheter tube thereof into a desired lung of a patient through an indwelling endotracheal tube while simultaneously accommodating voluntary respiration.

It is a further object of value to provide an aspirating device which confines contamination due to patient coughing during use of the device to the device itself.

It is another major object of this invention to provide structure for restraining a suction catheter tube of an aspirating of an aspirating/ventilating system in any desired extended position. It is a further paramount object to provide structure which substantially seals against entry of contaminants into a related collapsible envelope and also restrains a suction catheter tube of an aspirating or an aspirating/ventilating system in any desired extended position.

These and other objects and features of the present invention will be apparent from the detailed description taken with reference to the accompanying drawings.

BRIEF DESCRIPTION OF THE DRAWINGS

FIG. 2 is a perspective representation similar to FIG. 1, but showing the single use aspirating device as having been force-fit releasably connected to the exposed end of the indwelling endotracheal tube;

FIG. 3 is a perspective representation similar to FIG. 2 showing the catheter tube of the single use aspirating device as having been manually advanced into the respiratory system of the patient along the hollow interior of the endotracheal tube;

FIG. 4 is an enlarged cross-sectional view of the distal fitting of the aspirating device, taken along the lines 4—4 of FIG. 3;

FIG. 5 is an enlarged cross-sectional view of the proximal valve of the aspirating device, taken along lines 5—5 of FIG. 3;

FIG. 6 is a fragmentary perspective representation of a second, presently preferred proximal end valve usable with the aspirating device of FIG. 1;

FIG. 7 is an exploded perspective of the proximal end valve of FIG. 6;

FIG. 8 is a cross-section taken along lines 8—8 of FIG. 6;

FIG. 9 is a cross-section taken along lines 9—9 of FIG. 6;

DETAILED DESCRIPTION OF THE ILLUSTRATED EMBODIMENT

Removing secretions from the tracheobronchial tree is an integral part of the care given to patients who are intubated and receiving mechanical or other artificial ventilation. Secretions can be excessive in some respiratory disorders and constitute a serious threat to the persons having such respiratory disorders. The presence of an endotracheal tube is a hindrance to the patient's efforts to clear secretions through natural coughing. Suction catheters are used to clear secretions from the patient's airway.

Figure 1:
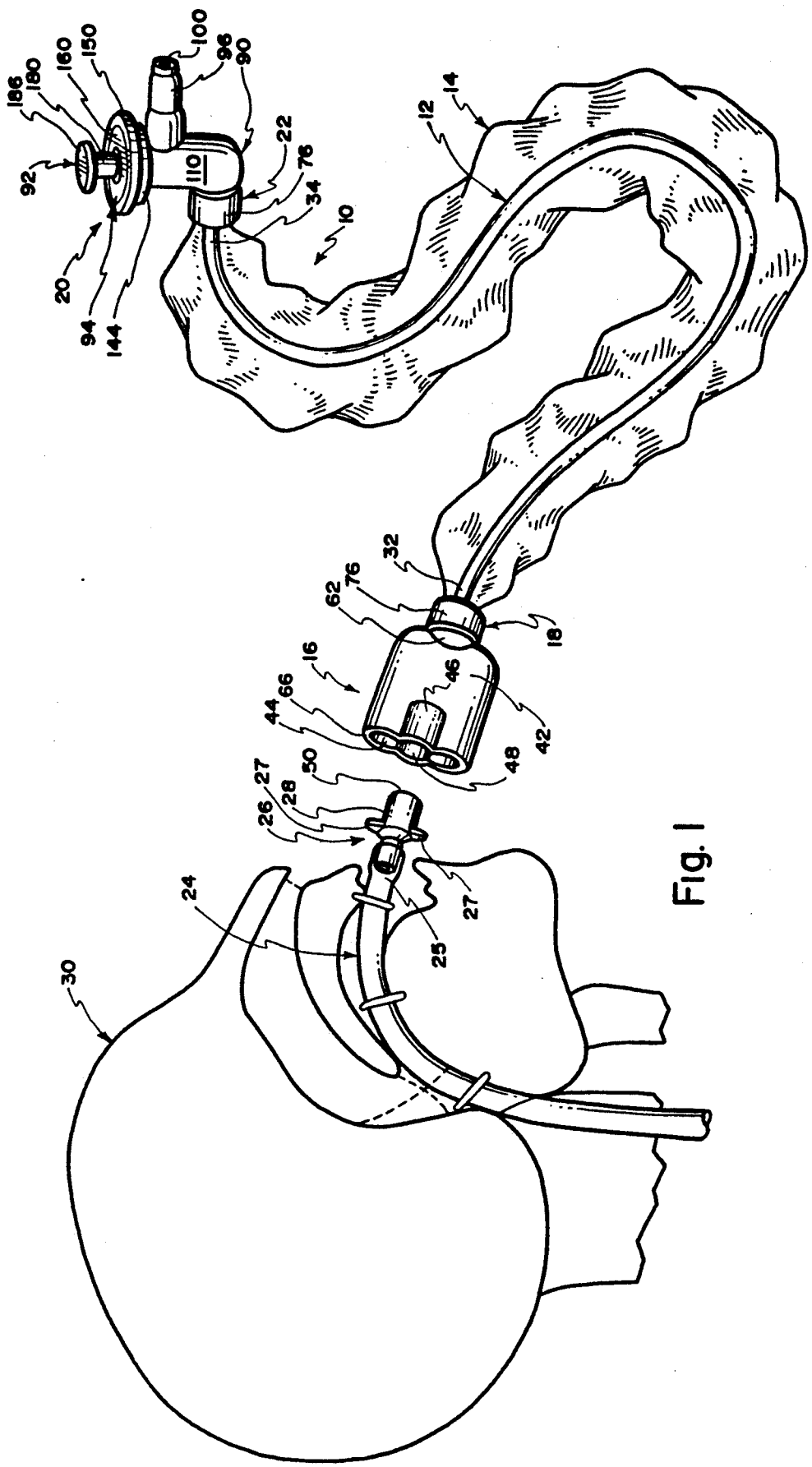
FIG. 1 is a perspective representation of a single use aspirating device, formed in accordance with the principles of the present invention illustrated in a detached relationship in respect to an endotracheal tube disposed in the throat of a patient.

Reference is now made in detail to the drawings where like numerals are used to designate like parts throughout. Particularly, FIG. 1 depicts a preferred single use aspirating device according to the present invention. The device is generally designated 10. The device 10 is intended for a single use and is not left connected or indwelling for repeated use over a protracted interval of time. The aspirating device 10 broadly comprises an aspirating catheter tube, generally designated 12, which extends along substantially the entire axial length of the device 10 and is encased within and substantially sealed by a transparent tube of flexible film comprising synthetic resinous material, such as medical grade polyethylene film. The tubular sleeve or envelope 14 prevents contamination of the encircled catheter tube 12. The envelope 14 is manually collapsed, typically between the thumb and index finger of the attending clinician or practitioner or the like in order to manipulate the catheter tube 12, as hereinafter more fully described.

The aspirating device 10 further comprises a fitting 16 disposed at the distal end of the device 10. The fitting 16 makes the present system an open system in that, when coupled to the exposed end of the endotracheal tube, voluntary respiration is accommodated through the interior of the bell-shaped, cough guard fitting 16 and the endotracheal tube. The distal end of the collapsible sleeve or envelope 14 is firmly secured and sealed to the fitting 16 by a force-fit collar 18.

The aspirating device 10 further comprises a normally closed manually operable valve, generally designated 20. Valve 20 is carried at the proximal end of the device 10 and is secured to the proximal end of the catheter tube 10. The proximal end of the collapsible sleeve or envelope 14 is firmly and sealingly secured to the valve 20 by an interference-fit collar, generally designated 22.

The aspirating device 10 is non-ventilating and intended to be releasibly and alignably joined to the exposed end of an indwelling endotracheal tube, generally designated 24, only at the time of use. The term "non-ventilating" is intended to mean having no capacity to force the patient to involuntarily ventilate. The device 10 is intended to be removed from the patient when a single use of the device 10 has been completed. The structure and the placement of the endotracheal tube 24 is conventional and requires no further description here. The endotracheal tube 24 is conventionally equipped with a fitting, generally designated 26, at the exposed proximal end thereof, which is force-fit into the proximal end 25 of the endotracheal tube 24 and presents central radially-extending tabs 27 and an exposed outwardly directed cylindrical extension 28. The fitting 26 has a hollow passage axially disposed along its interior. The endotracheal tube 24 is illustrated as having been properly placed through the mouth and the throat of a patient, generally designated 30.

The catheter tube 12 is controlled solely by manual manipulation thereof through the envelope and is at no time subject to mechanical manipulation. The aspirating catheter tube 12 has sufficient strength to prevent buckling, bending and twisting of the catheter tube which would otherwise occlude or tend to occlude the catheter tube. The aspirating catheter tube 12 is formed of a suitable synthetic resinous material, such as a medical grade transparent polyvinyl chloride and further comprises an annular wall essentially of uniform thickness throughout having uniform inside and outside diameters. The outside diameter is selected to comfortably pass through the endotracheal tube and throat and into either lung of the patient while accommodating simultaneous voluntary respiration by the patient through the hollow bell housing of the fitting 16 and the interior of the endotracheal tube.

The catheter tube 12 comprises a distal end 32, which is inserted into the lung of the patient 30. The distal end 32 is equipped with one or more intake ports 33 (FIG. 4) by which secretions existing within the lung of the patient may be drawn into the hollow interior of the catheter tube 12 and thence along the length thereof and across the valve 20, as hereinafter more fully explained. The proximal end 34 of the catheter tube 12 is anchored to the valve 20 in a manner explained in greater detail later.

The catheter tube 12 is adapted to be reciprocally and, if desired, rotationally displaced to and fro through the fitting 16 generally along the axis of the device 10 and along the axis of the endotracheal tube 26, for purposes yet to be more fully explained. The outside diameter of the catheter tube 12 is correlated with the transverse size of the passageway through the fitting 26 so that the distal end 32 of the catheter tube 12 can freely pass through the fitting 26 and along the hollow interior of the endotracheal tube 24.

Preferably the length of the flexible sleeve or envelope 14 is selected so that when in assembled condition, and with the envelope 14 fully extended, the distal tip of the catheter tube 12 will be disposed within the hollow interior of the fitting 16.

As best illustrated in FIG. 4, the fitting 16 is substantially hollow and comprises a body of material which extends axially but is transversely elongated in one plane only.

More specifically, the fitting 16, at the distal portion thereof comprises a flattened shell 40, illustrated as having a uniform wall thickness throughout, which defines an external surface 42 and a hollow interior 44. The shell is arcuately enlarged at opposed sites 46 and 48. The arcuate enlargements 46 and 48 together define a common interior diametrically enlarged opening therebetween which is substantially identical to the diameter of the projection 28 of the endotracheal fitting 26. Thus, the fitting 16 is force-fit at arcuate sites 46 and 48 over the projection 28 of the endotracheal fitting 26, as best illustrated in FIGS. 2 and 3. The nature of the interference fit is such as to permit intentional separation thereafter but to avoid inadvertent separation.

The distance to which the fitting 16 can be forced upon the projection 28 is limited by engagement of the outer edge 50 thereof (FIG. 1) with the interior shoulders 52 and 54 (FIG. 4) a the end of the wall enlargements 46 and 48 of the fitting 16. The shell 40 is convergently constricted at central site 56. The shell 40 there integrally emerges with a forwardly directed interior annular boss 58. Boss 58 extends into the hollow interior 44 of the shell 40 and has an inside uniform diameter at surface 60 which is substantially the same as the outside diameter of the catheter tube 12. Thus, bore 60 resists, at atmospheric pressure, entry of air or contaminants. However, when the catheter tube is advanced causing the envelope to be compressed, the above-atmospheric pressure within the envelope forces evacuation of the air within the envelope through the bore 60. One or more minute axially-directed grooves can be placed in the surface defining the bore 60 to provide for such evacuation, if desired. At the same time the catheter tube 12 can be manually reciprocated and rotated in respect to the surface 60. See FIG. 4. The fitting 16, because it is part of a single use device, is ordinarily not provided with structure by which the exterior surface of the catheter tube may be cleansed via irrigation as it is withdrawn from the respiratory system of the patient.

The shell 40 is also integral with a rearwardly directed generally annular projection 62. Annulus 62 terminates in a rearwardly exposed edge 64, while the shell 40 terminates in a forwardly exposed edge 66. The annulus 62 has an outside diameter at surface 68 and presents a generally hollow interior 70, surface 68 is interrupted by two closely spaced outwardly directed ribs 83 and 85. The annulus 62 is adapted for use in joining the fitting 16 to the distal end of the envelope 14 using the collar 18.

The collar 18 is preferably of polypropylene and essentially an annular ring comprising forward and rearward flat edges 72 and 74, each lying in a plane transverse to the axis of the fitting 16. The collar 18 further comprises an exterior arcuate surface 76 and a wall which is of substantially uniform thickness. The ring or collar 18 further comprises an interior generally annular surface 78, which is interrupted by one inwardly directed annular radial rib 82. The rib 82 is ultimately force-fit into the groove between annulus ribs 83 and 85. More specifically the ribs 82, 83 and 85 are sized, located and configured so that when the distal end of the envelope 14 is positioned essentially contiguously along the exterior surface 68 of the annulus 62, with the collar 18 circumscribing the envelope 14 slightly to the rear of the annulus 62, the collar 18 can be manually force-fit by axial displacement thereof over the top of the distal end of the envelope 14 and the annulus 62 so as to cause the annular rib 82 to be located between ribs 83 and 85 to compressively bite tightly against the envelope 14 in three closely spaced annular locations to secure and seal the envelope to the fitting 16, as illustrated in FIG. 4. As a consequence, bacteria and other contaminants are prevented from entering the flexible envelope prior to use and from leaving the envelope after use.

It is to be appreciated that the fitting 16 and collar 18 can be eliminated, where a highly simplistic economical aspirating device is desired. In that case the distal end 32 of the envelope 14 would be free prior to use with the catheter tube disposed within the envelope 14. To insert this type of device, the operator merely manually advances the distal end 32 of the catheter tube 34 out of the envelope 14 into the hollow of the endotracheal tube and thence into the desired lung of the patient.

With reference to FIG. 5, the aspirating manual control valve assembly 20 comprises a valve body generally designated at 90, a plunger, generally designated at 92 and a valve member, generally designated 94, for which functions both as a seal and as a return spring. Valve 20 is not vented at any time to the atmosphere.

The valve body 90 is preferably of one piece molded construction and comprises an axial nipple 96, which is press fit connected to a hose or the like and thence to a conventional vacuum source 98 (FIGS. 2 and 3). Preferably, body 90 is formed of ABS. The nipple 96 has a hollow interior 100, shown as being of uniform cylindrical diameter. The nipple 96 comprises a stepped exterior comprising a larger diameter portion 102 and a smaller diameter proximal portion 104. A tapered shoulder 96 integrally joins the cylindrical surface 102 and 104 at essentially a central location.

The cylindrical portion 102 joins a transverse hollow body portion 108 which comprises a cylindrical wall 110. Wall 110 defines a hollow cylindrical interior 112. The hollow interior 112 of the transverse wall 108 is normal and opens into the hollow bore 100 of the nipple 96.

The transverse wall 110 merges with a forwardly directed annulus 114. The wall of the annulus 114 is enlarged at one side at abutment 116, which defines shoulder 118. The wall of annulus 114 essentially closes one end of the bore 112. Wall of annulus 114 terminates in an edge 122. Concentrically within the wall of annulus 114 is disposed a boss 124. A hollow interior 120 is defined within the boss 124. The hollow of the catheter tube 12 are in open communication with the hollow interior 120 of the annulus.

The interior diameter of the boss, at site 126 is substantially the same in diameter as the outside diameter of the catheter tube 12. The catheter tube, as illustrated in FIG. 5, is placed concentrically within the hollow 120 and secured by suitable bonding agent, adhesive or the like at site 126. Thus, the proximal end of the catheter tube 12 is rigidly anchored to the valve 20. Accordingly, the hollow interior of the catheter tube 12 is directly in fluid communication with one end of the hollow bore 112 of the wall 110. The wall 110 integrally merges with the boss 124, the boss terminating in a cantilevered edge 128 also disposed in a plane transverse to the axis of the catheter tube 12.

The annulus 114 comprises an external cylindrical surface 130, which is interrupted by a radially-directed outwardly-projecting rib 82'. When the proximal end of the sleeve or flexible envelope 14 is contiguously placed along the outside surface 130, with the collar 22 surrounding the envelope 14 to the left of the annulus 114 (as viewed in FIG. 5), the ring or annulus 22, which is substantially similar to collar 18 and has been so numbered, is displaced and thereby caused to be force-fit over the proximal end of the envelope 14 causing internal ribs 83' and 85' of the collar to be located on opposite sides of the ribs 82'. Thus, the three closely spaced ribs compressively bite against the contiguous portion of the envelope 14 and force the same tightly against the surface 130 of the annulus 114. In this way the envelope 14 is firmly secured and sealed against to the valve 20 against inadvertent release.

The transverse cylindrical wall 110, at the end thereof opposite abutment wall 116, terminates in a radially directed cup-shaped flange 140. Flange 140 serriatum comprises an exposed annular surface 142 which joins surface 108, a shoulder 144, a further annular surface 146 and an arcuate edge 148. The edge 148 and the annular surface 146 comprise part of an annular lip 150 disposed parallel to the bore 112.

The lip 150 terminates in a transversely directed edge 152. Edge 152 merges through 90 degrees into an annular surface 154, which in turn merges through 90 degrees with a flat surface 156. Surface 156 merges with the wall 110 at the transverse bore 112. Surface 154 and 156 create a dish-shaped recess. Surface 156 also is interrupted by an annular recessed groove 158.

The recess in the described flange, formed by surfaces 154 and 156 receives part of a valve member comprising seal/spring member 94. More specifically, the seal/spring member 94 comprises a flange 160, which is sized and shaped to be contiguously received at wall surfaces 154 and 156 and within groove 158 in such a fashion that the upper surface thereof is flush with edge surface 152. A suitable adhesive or the like can be placed at the interface between the flange 140 of the valve body 90 and the flange 160 of the seal/spring member 94 to secure the two components together. The flange 160 has a central opening at site 162.

The seal/spring member 94 is preferably made of highly resilient, relatively soft synthetic material, such as silicone rubber which has a significant memory to accommodate the required sealing and spring functions. The seal/spring member 94 comprises a hollow annulus 164 which integrally merges with the flange 160 and comprises an inside circular diameter at surface 166 and an outside diameter at cylindrical surface 168.

The diameter at surface 166 is the same size and aligned with the central opening 162 in flange 160. The diameter of the outside cylindrical surface 168 is less than the diameter of the bore 112 of the valve body cylindrical wall 110. This creates an annular space between the surfaces 112 and 168. The cylindrical wall 164 integrally merges, at a location remote from the flange 160 with a piston head 170. The piston wall 170 is integral with the cylindrical wall 164, being formed as one piece therewith and comprises a blunt exposed end 172 and an annular edge 174. Together walls 164 and 170 define a blind bore the diameter of the annular edge 174 in a non-stress condition is enlarged, being slightly larger than the diameter of the bore 112 so that the piston wall 170 at edge 174 is force-fit into the position illustrated in FIG. 5.

The position of FIG. 5 is the non-actuated, normally closed, unstressed condition of the valve 20. Thus, it can be seen that the length of the cylindrical wall 164 is selected so that the piston wall and the seal thereof is disposed reciprocally but sealingly against the interior surface of the wall 110 of bore 112 at a site between the hollow interior 100 of the nipple 96 and the hollow interior 120 of the boss 124. Thus, in the unstressed, at rest condition illustrated in FIG. 5, the valve 20 prevents vacuum available at source 98 from reaching the interior of the catheter tube 12. The valve arrangement in this condition and position and in all other positions is sealed and unvented which prevents entry of contaminants into the hollow of the catheter tube or into the hollow of the envelope 14.

The plunger 92 comprises an elongated cylindrical extension 180, which comprises a blunt edge 182 and an exposed end which is integrally connected at site 184 to a disc-shaped handle or actuator 186. The exterior diameter of the cylinder 180 is selected so as to be slightly larger than the at rest interior diameter at surface 166 of the wall 164. Accordingly, when the cylinder 180, made of rigid plastic material, is inserted into the blind bore created by the cylindrical wall 164 and the piston wall 170, a stretch-fit relationship is created wherein the material of the wall 164 radially compressively grips the cylinder 180.

When the clinician, or doctor grasps the catheter tube 14 between the fitting 16 and the valve 20 by collapsing the envelope 14 upon the catheter tube, with the device 10 connected to the endotracheal tubes as illustrated in FIG. 2, the clinician manually advances the catheter tube through the fittings 16 and 26 and down the endotracheal tube 24 into one of the lungs of the patient. With the distal end of the catheter tube 12 properly positioned in the selected lung so that the port or ports 33 thereof are placed appropriately in accumulated secretions in the lung. With the valve 20 appropriately conventionally connected to the vacuum source 98, the secretions are evacuated from the lung through the hollow interior of the catheter tube 32 and the valve 20 when the operator depresses the actuator 186 from the position illustrated in solid lines in FIG. 5 to the position illustrated in dotted lines in FIG. 5, counter to the memory of the material from which the seal/spring member 94 is formed. This fluid-connects the hollow bore 112 to both the hollow 100 of the nipple 96 and hollow 120 of the boss 124. Thus, the force of the vacuum from source 98 is communicated to the hollow interior of the catheter tube 12. The valve 20 is completely sealed against loss of the vacuum pressure applied to the lung of the patient.

When the secretions within the lung have been appropriately evacuated, the second lung can be evacuated in a similar fashion, if desired. In any event, when a single use of the device 10, either in one or both lungs, has been completed, the user releases the valve actuator 186 causing the memory of the seal/spring member 94 to return the valve 20 to its normally closed position. The catheter tube 12 is then manipulated by collapsing the envelope 14 upon the catheter tube, will remove the catheter tube 12 from the endotracheal tube 24 until the full length of the catheter tube 12 is substantially disposed within the envelope 14. The fitting 16 is axially removed from the endotracheal projection 28 and the valve 20 is disconnected from the vacuum source 98. The device 10 is then discarded.

Coughing by the patient during use of the device 10 does not contaminate areas outside the aspirating device per se.

In lieu of the valve fitting 20, the valve fitting illustrated in FIGS. 6-9 may be utilized. This valve fitting is generally designated 200. The valve fitting 200 comprises a valve body 201, a valve member 270 and a retainer cap 272. See FIG. 7. The valve body 201, preferably formed as one piece by injection molding, comprises a first cantilevered end 202 by which one end of the envelope 14 is secured at collar 22. End 202 of the valve fitting 200 is identical to the end of the valve fitting 20 which connects to the envelope 34 at collar 22, as illustrated in FIGS. 1-3 and 5. End 202 is correspondingly numbered in FIGS. 6-9. Accordingly, no further description of end 202 of fitting 200 is needed.

The valve body 201 comprises a central portion 204, which defines a linear passageway 206, centrally located and axially directed. Passageway 206 is aligned with and is illustrated as having a diameter substantially the same as the interior diameter of the catheter tube 34. Axial passageway 206 is subdivided into two sequential sections by a vertically-directed rectangular slot 208. Vertically-directed, rectangular slot 208 comprises an opening 210 at top surface 212 of the central portion 204. Surface 212 is essentially circular and forms the bottom of a deflection chamber or compartment 214, as explained hereinafter in greater detail.

The slot 208 is vertically elongated and extends, as illustrated in FIG. 8, downwardly to a location substantially below the end 202 of the valve fitting 200. The rectangular slot 208 has a predetermined uniform thickness 234 (FIG. 8) and a downwardly tapered width 236 (FIG. 9). The interior bottom surface of the vertical rectangular slot 208 comprises part of a rectangular horizontally-directed wall 218. Wall 218 terminates in exposed rectangular exterior surface 220 and merges with vertically directed transverse walls 222 and 224 and downwardly tapered side walls 223 and 225, respectively. The wall 222 is defined by an interior surface 226 and an exterior surface 228. Wall 224 is defined by interior surface 230 and exterior surface 232. Wall 223 comprises interior surface 235 and exterior surface 237. Wall 225 comprises interior wall surface 233 and exterior wall surface 231. As illustrated, the walls 218, 222, 224, 223 and 225 are illustrated as being of uniform thickness throughout.

Preferably, the valve body member 201 is injection molded of shape-retaining synthetic resinous material, such as rigid ABS.

The relatively massive central portion 204 comprises an integral upwardly directed annular ring or boss 240. Boss 240 comprises an annular wall 242, illustrated as being of substantially uniform thickness throughout. Wall 242 comprises an annular interior surface 244, forming part of the deflection chamber or compartment 214, and an external surface 243, which is generally cylindrical but interrupted by a horizontally-directed radial lip 246, illustrated as being generally of rectangular cross-section. Annular wall 242 terminates in a blunt upper edge 247.

The relatively massive central portion 204 also comprises a proximal end portion, generally designated 250. End 250 is cantilevered generally away from the patient from the central portion 204 and centrally defines the longer of the two sections of the axial bore 206. The external surface of the end 250 comprises a series of stepped annular sections to provide a better grip when tubing connected to a vacuum source is force-fit over the exterior of the fitting 250. These stepped annular surfaces are sequentially designated by the numerals 252, 254, 256 and 258, respectively. Radially directed shoulders 260, 262 and 264 are respectively interposed seriatum between the indicated annular surfaces 252, 254, 256 and 258. The end 250 terminates in a blunt transversely-directed edge 266.

The valve member 270 functions not only to open and close the valve fitting 200 but acts as its own return spring. Valve member 270 is formed of silicone rubber or the like which has characteristics of substantial elasticity, substantial memory and substantial compressibility. Valve member 272 comprises an inverted cup-shaped spring member 274. Spring member 274 comprises a disc-shaped diaphragm top 275 which comprises a top surface 276 and a bottom surface 278. The disc-shaped top 275 is illustrated as being of uniform thickness. Disc-shaped top 275 merges at its perimeter with a downwardly-directed annular flange or lip 280, illustrated as being of uniform thickness throughout and comprising outside and inside wall surfaces 281 and 283. The lip 280 is the structure by which the valve member 270 is held in the assembled position illustrated in FIG. 8. The disc-shaped top 275 specifically functions as a diaphragm return spring.

Integral with the disc-shaped top 275 is a centrally-disposed upwardly-projecting cylindrical actuator 282. Actuator 282 terminates in a blunt exposed upper edge 284 and has enough mass and structural integrity so that it does not deflect from side-to-side when depressed.

Also integral with the disc-shaped top 275 is a downwardly directed generally rectangular flat valve plate 286. Valve plate 286 comprises front and back flat surfaces 288 and 290, an edge 292 which runs through 180 degrees from and to bottom surface 278. The edge 292 comprises rounded corners 294 and 296 adjacent the downwardly-directed apex 298 of the edge 292.

The valve plate 286 also comprises an aperture 300 of predetermined size and location spanning between the surfaces 288 and 290. As illustrated, the aperture 300 may be located essentially equidistant between the disc surface 278 and the end 298.

The width end thickness of the valve plate 286 are predetermined so as to be just slightly less than the thickness 234 and slightly less than the width 236 of the slot 208. The vertical length of the valve plate 286 is, in an unstressed state, formed so as to extend only partly along the length of the slot 208 so that the aperture 300 is clearly out of alignment with the bore sections 206 and the valve plate 286 is axially compressed. The dimensional relationship between the valve plate 286 and the slot 208 is, therefore, such that a seal is created between the surface 290 of the valve plate 286 and the slot surface 230. Thus, when the valve plate 286 is in the unstressed position illustrated in FIG. 8, any vacuum pressure within the bore 206 at the end 250 is isolated by the valve plate 286 from the interior of the catheter tube 34.

The retainer cap 272 is preferably formed of shaped-retaining synthetic resinous material and comprises an upper, horizontally disposed wall 310 of uniform thickness comprising a top surface 312 and a bottom surface 314. The wall 310 is interrupted by central aperture 316, the diameter of which is larger than the diameter of the cylindrical actuator 282 so that the actuator 282 may reciprocate up and down loosely through the aperture 316. The horizontal wall 310 merges with an annular downwardly directed flange 320 which is integral with the annular wall 310 and extends radially downwardly and comprises exposed annular surface 322 and interior generally annular surface 324. An annular groove 326 is disposed in a wall 320 at surface 324 near the lower edge 328, and sized and located so as to snugly fit over the flange 246 and retain the retainer 272 in a snap-fit assembled position as illustrated in FIG. 8 against inadvertent removal. This retains the wall 280 of the valve member 270 in its assembled condition.

Note that downwardly-directed radial flange 280 is sized and shaped to fit compressively between the space created between the walls 242 and 320 with the deflectible disc-shaped top 275 spanning across the cavity 214. Thus, the downward flange or lip 280 is trapped and held in the assembled position by the retainer cap 272 against inadvertent release.

The length of the cylindrical actuator 282 is preferably selected so that manual depression of the same (against the memory of the silicone rubber material from which the disc-shaped top spring member 275 is made) may continue downwardly until the upper blunt surface 284 is essentially flush with the surface 312 of the retainer 272. This forces the valve plate 286 downwardly into the slot 208 a distance sufficient to bring the aperture 300 of the valve plate 286 into alignment with the two bore segments 206. Thus, the vacuum is communicated through the two bore sections 206, the aperture 300 and the hollow interior of the catheter tube 34 to remove secretions from a selected lung of the patient.

Release of air within the chamber 214 and the lower portion of the slot 208 during the mentioned actuation is accommodated along the edges of the valve plate 286. Also, the valve 200, being a normally closed valve and being entirely manually operable, means that the valve is in its "on", depressed condition only so long as manual pressure is retained at the actuator 282. Thus, the operator will maintain the application of the vacuum pressure to the hollow interior of the catheter tube for removal of secretions from the selected lung, only so long as the procedure is efficacious for such removal. When the secretions have been removed, the operator merely releases the actuator 282 and the memory of the material from which the disc-shaped top spring member 275 is made will cause the valve member 270 to return to the unstressed, at rest position illustrated in FIGS. 8 and 9. When the catheter tube is removed from the respiratory system, the fitting 16, if part of the device, is uncoupled from the endotracheal tube and the aspirating device discarded.

Figure 10:
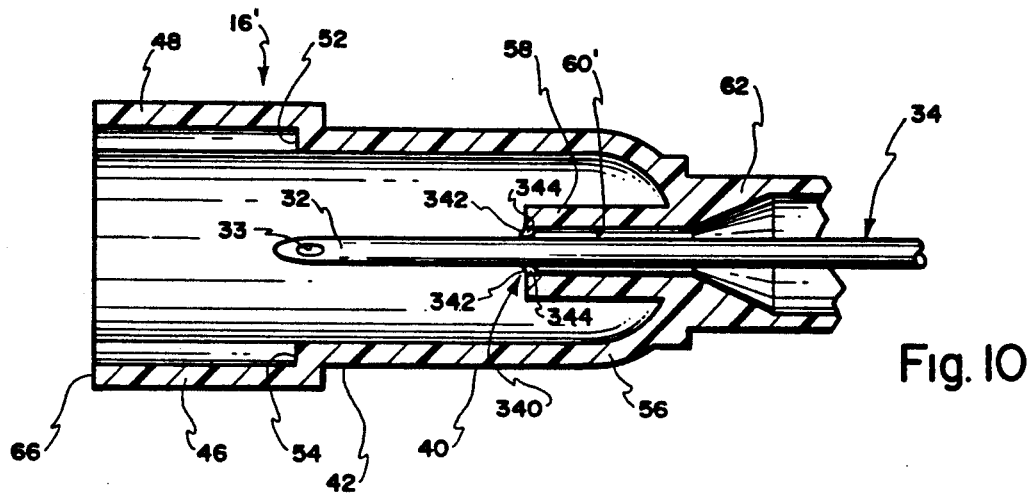
FIG. 10 is an enlarged fragmentary section of a modified distal end fitting equipped with structure which grips the exterior of the catheter tube to restrain it in any desired extended position in respect to the distal end fitting.
Figure 11:
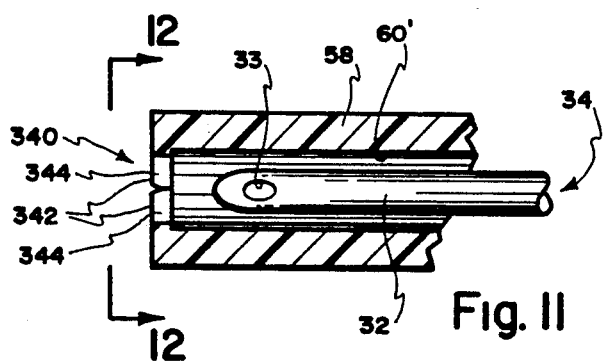
FIG. 11 is a fragmentary section of the distal end fitting of FIG. 10, showing the catheter tube retracted from the gripping structure.
Figure 12:
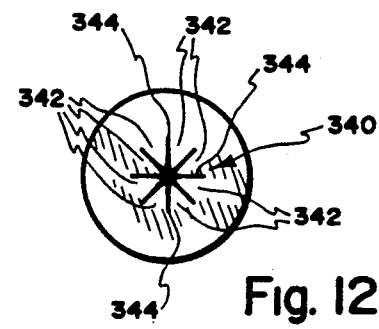
FIG. 12 is an end view of the gripping structure taken along lines 12—12 of FIG. 11.

Reference is now made to FIGS. 10-12 which illustrate gripping structure, generally designated 340. Gripping structure 340 comprises part of the distal end fitting 16', which is substantially identical to distal end fitting 16, shown FIG. 4, and heretofore described. Those parts of fitting 16' which are identical to the corresponding parts of fitting 16 has been so designated by numerals in FIGS. 10-12. The bore 60' is somewhat larger than the illustrated bore 60 of fitting 16 so that a substantially loose concentricity will exist between the distal end 32 of the catheter tube 34 and the bore 60', when the catheter tube is within the bore 60' either retracted or extended.

The gripping structure 340 comprises a series of angular fingers 342, which are created by a series of radially-directed slits 344, as best illustrated in FIG. 12. Thus, the fingers 342, being formed of relatively thin, yieldable thin synthetic resinous material, preferably as one piece with fitting 16', may be forcibly displaced from the radially-disposed, unstressed orientation of FIG. 12 to the essentially axially-disposed deflected orientation of FIG. 10. In the orientation of FIG. 10, the slits 344 open so that air from within the associated collapsible envelope 14 is readily evacuated as the catheter tube 34 is advanced through the housing 16' and the hollow of the endotracheal tube into the respiratory system of the patient. However, the fingers 342, because of the memory of the material from which each is formed, collectively exert a radially-directed compressive force upon the exterior surface of the catheter tube 34 while at the same time frictionally engaging the exterior surface of the catheter tube 34. Thus, the clinician, doctor or the like, responsible for manipulating the catheter tube 34 may advance, or retract the catheter tube 34 to a precise extended position through the gripping structure 340 and the fingers 342, thereafter, will retain the catheter tube 34 in the selected, extended position against inadvertent relative displacement of the catheter tube 34 in respect to the fitting 16'.

As best illustrated in FIGS. 11 and 12, the gripping structure 340 essentially closes into a substantially sealed, radially-directed composite structure prior to the advancement of the catheter tube 34 and after retraction of the catheter tube as well. Thus, the gripping structure 340, when closed as illustrated in FIGS. 11 and 12, functions to substantially seal against undesired entry of contaminants into the hollow of the collapsible envelope 14.

Figure 13:
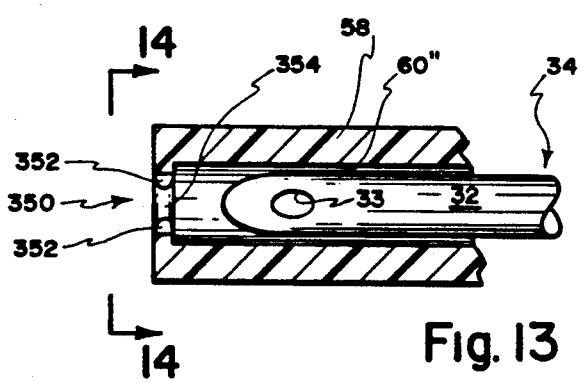
FIG. 13 is a fragmentary section similar to FIG. 11, showing a modified form of the gripping structure.
Figure 14:
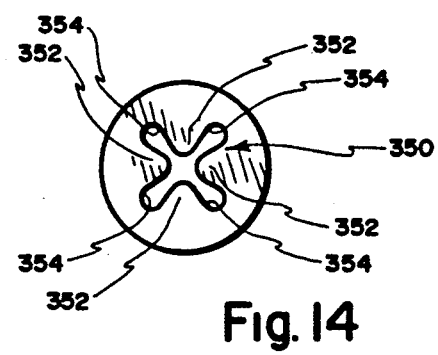
FIG. 14 is an end view taken along lines 14—14 of FIG. 13.

Reference is now made to FIGS. 13 and 14 which illustrate a modified gripping structure, generally designated 350. Gripping structure 350 comprises a plurality of rounded fingers 352, which are spaced one from another in their unstressed radial orientation by open slots 354. The fingers 352 function in substantially the same fashion as previously described fingers 342. However, with the existence of the open slots 354, the gripping structure 350 does not per se form a seal when the catheter tube 34 is withdrawn or prior to its advancement. Accordingly, it is preferred that the central bore 60" have a diameter just slightly greater than the diameter of the catheter tube so that entry of contaminants between the two is either prevented or substantially alleviated.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. A single use aspirating vacuum pressure assembly having a distal end comprising:

a hollow aspirating catheter tube comprising a proximal end;

a flexible envelope generally surrounding the catheter tube and comprising a distal end;

a fitting at the distal end of the assembly comprising means for temporarily releasibly connecting the distal end of the assembly to an indwelling tracheal tube means providing an orifice through which the catheter tube is alignedly passed into and out of the tracheal tube and means connected to the distal end of the envelope;

normally closed valve structure by which aspirating vacuum pressure is selectively communicated to the interior of the catheter tube for evacuation of lung secretions, the valve structure comprising valve means and valve body means in which at least part of the valve means may be manually displaced, the valve body means comprising normally closed bore means for connection at opposite ends of the bore means respectively to the proximal end of said catheter tube and to a source of the vacuum pressure, the valve means comprising a single one-piece structural element comprising one portion sealing joined to the valve body means for preventing entry of atmospheric air into the valve structure, a second portion self-biasing the structural element toward a normally closed position at the bore means, a third portion sealing the valve means to the valve body means against flow beyond the bore means within the valve structure caused by vacuum pressure, a manual displaceable fourth valving portion comprising flow path-defining means by which the bore means are caused to be opened for flow caused by the vacuum pressure across the valve structure when the valving portion is displaced counter to the self-biasing into an open position;

exposed actuator means joined to at least one portion of the valve means.

2. A single use aspirating vaccum pressure assembly comprising:

a hollow aspirating catheter tube comprising a proximal end;

a flexible envelope generally surrounding the catheter tube and comprising a distal end;

a fitting at a distal end of the assembly comprising means for temporarily releasibly connecting the distal end of the assembly to an indwelling tracheal tube, means providing an orifice through which the catheter tube is alignedly passed into and out of the tracheal tube and means connected to the distal end of the envelope;

normally closed valve structure by which aspirating vacuum pressure is selectively communicated to the interior of the catheter tube for evacuation of lung secretions, the valve structure comprising valve means and valve body means in which at least part of the valve means may be manually displaced, the valve body means comprising normally closed bore means for connection at opposite ends of the bore means respectively to the proximal end of said catheter tube and to a source of the vacuum pressure, the valve means comprising a single one-piece structural element comprising one portion sealing joined to the valve body means for preventing entry of atmospheric air into the valve structure, a second portion self-biasing the structural element toward a normally closed position at the bore means, a third portion comprising cylindrical means sealing the valve means to the valve body means against flow beyond the bore means within the valve structure caused by vacuum pressure, a manual displaceable fourth valving portion comprising flow path-defining means by which the bore means are caused to be opened for flow caused by the vacuum pressure across the valve structure when the valving portion is displaced counter to the self-biasing into an open position.

3. A single use aspirating vacuum pressure assembly comprising:

a hollow aspirating catheter tube comprising a proximal end;

a flexible envelope generally surrounding the catheter tube comprising a distal end;

a fitting at a distal end of the assembly comprising means for temporarily releasibly connecting the distal end of the assembly to an indwelling tracheal tube, means providing an orifice through which the catheter tube is alignedly passed into and out of the tracheal tube and means connected to the distal end of the envelope;

normally closed valve structure by which aspirating vacuum pressure is selectively communicated to the interior of the catheter tube for evacuation of lung secretions, the valve structure comprising valve means and valve body means in which at least part of the valve means may be manually displaced, the valve body means comprising normally closed bore means for connection at opposite ends of the bore means respectively to the proximal end of said catheter tube and to a source of the vacuum pressure, the valve means comprising a single one-piece structural element comprising one portion sealing joined to the valve body means for preventing entry of atmospheric air into the valve structure, a second portion self-biasing the structural element toward a normally closed position at the bore means, a third portion sealing the valve means to the valve body means against flow beyond the bore means within the valve structure caused by vacuum pressure, a manual displaceable fourth valving portion comprising diametrically reduced means and flow path-defining means by which the bore means are caused to be opened for flow caused by the vacuum pressure across the valve structure when the valving portion is displaced counter to the self-biasing into an open position.

4. A single use aspirating vacuum pressure assembly comprising:

a hollow aspirating catheter tube comprising a proximal end;

a flexible envelope generally surrounding the catheter tube comprising a distal end;

a fitting at a distal end of the assembly comprising means for temporarily releasibly connecting the distal end of the assembly to an indwelling tracheal tube, means providing a pathway through which the catheter tube is alignedly passed into and out of the tracheal tube and means connected to the distal end of the envelope;

normally closed valve structure by which aspirating vacuum pressure is selectively communicated to the interior of the catheter tube for evacuation of lung secretions, the valve structure comprising valve means and valve body means in which at least part of the valve means may be manually displaced, the valve body means comprising normally closed bore means for connection at opposite sides of the bore means to the proximal end of said catheter tube and to a source of the vacuum presence, the valve means comprising a single one-piece structural element comprising one portion comprising an annular lip sealing joined to the valve body means for preventing entry of atmospheric air into the valve structure, a second portion self-biasing the structural element toward a normally closed position at the bore means, a third portion sealing the valve means to the valve body means against flow beyond the bore means within the valve structure caused by vacuum pressure, a manual displaceable fourth valving portion comprising flow path-defining means by which the bore means are caused to be opened for flow caused by the vacuum pressure across the valve structure when the valving portion is displaced counter to the self-biasing into an open position.

5. A single use aspirating vacuum pressure assembly comprising:

a hollow aspirating catheter tube comprising a proximal end;

a flexible envelope generally surrounding the catheter tube the envelope comprising a distal end;

a fitting at a distal end of the assembly comprising means for temporarily and releasibly connecting the distal end of the assembly to an indwelling tracheal tube, means defining a pathway through which the catheter tube is alignedly passed into and out of the tracheal tube and means connected to the distal end of the envelope;

normally closed valve structure by which aspirating vacuum pressure is selectively communicated to the interior of the catheter tube for evacuation of lung secretions, the valve structure comprising valve means and valve body means in which at least part of the valve means may be manually displaced, the valve body means comprising normally closed bore means and means for connecting the valve body means to the proximal end of said catheter tube, the valve means comprising a structural element of one-piece construction comprising means sealing a portion of valve means to the valve body means for preventing entry of atmospheric air into the valve structure, means self-biasing the structural element toward a normally closed position, means sealing the valve means to the valve body means against fluid flow beyond the bore means within the valve structure caused by vacuum pressure and manual displaceable valving means comprising flow path-defining means by which the bore means are caused to be opened for flow caused by the vacuum pressure across the valve structure when the valving means are displaced by manual force counter to the self-biasing into an open position.

6. A device according to claim 5 wherein the structural element of one-piece construction comprises a fifth portion comprising exposed actuator means by which the structural element is manually displaced from the closed to the open position counter to the self-biasing.

7. A device according to claim 5 wherein the first mentioned sealing means comprise flange means.

8. A device according to claim 7 further comprising cap means for compressively holding the flange means in joined sealed relation with the valve body means.

9. A device according to claim 5 wherein the self-biasing means comprise diaphragm means.

10. A device according to claim 5 wherein the third portion comprises plate means.

11. A device according to claim 5 wherein the second mentioned sealing means comprise aperture means.

12. A device according to claim 5 wherein the structural member of one-piece construction comprises silicon rubber.

13. A single use disposable aspirating device, for use with an indwelling tracheal tube having a hollow interior and an exposed hollow male fitting, the aspirating device comprising:

an aspirating catheter tube;

a manually collapsible flexible envelope substantially surrounding the catheter tube;

fitting means carried at the distal end of the device, the fitting means comprising (a) female receptacle means for temporarily and releasibly attaching the device to the exposed male fitting of the indwelling tracheal tube, (b) means defining a voluntary respiratory flow path for gasses through the fitting means between the atmosphere and the hollow interior of the male fitting of the tracheal tube, (c) hollow male means sealingly connected to the distal end of the collapsible flexible envelope, (d) internal passageway means sized, shaped and adapted to accommodate snug receipt and reciprocable passage therethrough of the catheter tube into and from the respiratory system of the patient;

normally closed vacuum pressure manual control valve assembly means connected at the proximal end of the device, the aspirating control valve assembly means comprising the body means comprising (a) means sealingly connected to the proximal end of the collapsible flexible envelope, (b) hollow means to which the proximal end of the catheter tube is connected, (c) first passageway means through which vacuum pressure from a source is in fluid communication to a normally closed valving member within the interior of the valve body means, (d) second passageway means by which the hollow of the catheter tube is in fluid communication to the valving member, the valve assembly means further comprising normally closed manually operable valve means comprising exposed manual actuator means associated with the normally closed valving member, the valving member being disposed displaceably in the valve body means between said first and second passageway means normally preventing the vacuum pressure from reaching the interior of the catheter tube, the valving member when manually disposed to and manually retained at a second position by the exposed actuator, permitting the vacuum pressure to cross between the first and second passageway means at the valving member and reach the interior of the catheter tube to evacuate accumulated secretions from the lungs of a medical patient.

14. An aspirating device according to claim 13, wherein the hollow male means of the fitting means comprises a hollow annulus connected to the distal end of the flexible envelope by an external force-fit collar compressively superimposed upon the distal end of the flexible envelope and the outside of the annulus.

15. An aspirating device according to claim 13 wherein the passageway means of the fitting means are sized and shaped to substantially prevent entry of contaminants into the envelope at the fitting means while accommodating release of air within the envelope as the catheter tube is advanced through the fitting means, the fitting means being aligned with the hollow of the exposed hollow male fitting of the tracheal tube.

16. An aspirating device according to claim 13, wherein the actuator means and the normally closed valving member are associated together by self-bias means having memory, the memory of the self-bias means urging the valving member towards the normally closed position, the self-bias means being integrally formed with the valving member whereby displacement of the valving member by actuation of the actuator means from the normally closed to open position stretches the self-bias means counter to said memory and release of the actuator means allows the memory of the self-bias means to return the valving member to the normally closed position.

17. An aspirating device according to claim 13 wherein the control valve assembly means comprise three pieces, the three pieces comprising the valve body means, the actuator means and the valve means exclusive of the actuator means.

18. An aspirating device according to claim 13 wherein the valve body means comprise a single piece and the valve means comprise a single piece comprising (a) said actuator means, (b) said valving member, (c) means by which a portion of the valve means are connected to the valve body means for preventing entry of atmospheric air and accommodating displacement of the valving member, and (d) said self-bias means by which the valve member is returned to its normally closed position upon manual release of the actuator means.

19. A method of aspirating secretions from a lung of a medical patient using a hollow aspirating catheter tube comprising the steps of:

releasibly and temporarily connecting a distal end fitting of an aspirating assembly to an exposed hollow end piece of a hollow indwelling tracheal tube so as to accommodate voluntary inhalation of atmospheric air and exhalation of gas by a medical patient through the distal end fitting;

advancing a distal end of the hollow aspirating catheter tube of the aspirating assembly through the distal end fitting, the hollow of the exposed end piece and the hollow of the tracheal tube into an evacuation position in a lung while continuing to accommodate voluntary breathing of atmospheric air by the patient through the distal end fitting;

selectively delivering negative pressure across a normally closed valve at the proximal end of the aspirating assembly through the hollow interior of the hollow aspirating catheter tube to the distal end of the hollow aspirating catheter tube by manual displacement of a valve actuator from a closed to an open position to evacuate secretions from the lung;

manually maintaining the valve actuator in open position counter to a bias so long as said evacuation is desired;

manually releasing the valve actuator which returns the normally closed valve to the normally closed position responsive to said bias to terminate said evacuation;

manually withdrawing the hollow aspirating catheter tube from the tracheal tube and the exposed hollow end piece of the tracheal tube into the aspirating assembly;

thereafter disconnecting the distal end fitting from the exposed hollow end piece of the tracheal tube;

discarding the aspirating assembly.

* * * * *